United States Patent
Hommann

(10) Patent No.: US 7,879,007 B2
(45) Date of Patent: Feb. 1, 2011

(54) INJECTION DEVICE GUIDE SPRING

(75) Inventor: Edgar Hommann, Grossaffoltern (CH)

(73) Assignee: TecPharma Licensing AG, Burgdorf (CH)

( * ) Notice: Subject to any disclaimer, the term of this patent is extended or adjusted under 35 U.S.C. 154(b) by 267 days.

(21) Appl. No.: 11/840,494

(22) Filed: Aug. 17, 2007

(65) Prior Publication Data
US 2008/0077084 A1 Mar. 27, 2008

Related U.S. Application Data

(63) Continuation of application No. PCT/CH2006/000017, filed on Jan. 11, 2006.

(30) Foreign Application Priority Data

| Feb. 18, 2005 | (DE) | .................... 20 2005 006 333 U |
| Mar. 10, 2005 | (DE) | .................... 20 2005 003 847 U |
| Apr. 15, 2005 | (DE) | ........................ 10 2005 017 477 |

(51) Int. Cl.
*A61M 5/20* (2006.01)
*A61M 5/32* (2006.01)

(52) U.S. Cl. .................... 604/136; 604/135; 604/198

(58) Field of Classification Search ................ 604/131, 604/134–136, 187, 82, 191, 232, 198
See application file for complete search history.

(56) References Cited

U.S. PATENT DOCUMENTS

| 1,039,591 | A |   | 9/1912 | Prideaux |
| 1,817,652 | A |   | 8/1931 | Smith |
| 2,866,458 | A |   | 12/1958 | Hein, Jr. |
| 4,064,879 | A |   | 12/1977 | Leibinsohn |
| 6,099,503 | A | * | 8/2000 | Stradella ..................... 604/135 |
| 7,297,136 | B2 | * | 11/2007 | Wyrick ........................ 604/117 |
| 2001/0019189 | A1 |   | 9/2001 | Meier et al. |
| 2004/0024367 | A1 |   | 2/2004 | Gilbert |

FOREIGN PATENT DOCUMENTS

| DE | 7340029 U | 5/1975 |
| EP | 0577448 A1 | 1/1994 |
| GB | 16069 A1 | 0/1910 |
| GB | 301075 A1 | 10/1929 |

* cited by examiner

*Primary Examiner*—Nicholas D Lucchesi
*Assistant Examiner*—Nathan R. Price
(74) *Attorney, Agent, or Firm*—Dorsey & Whitney LLP; David E. Bruhn, Esq.

(57) ABSTRACT

An injection appliance including a housing, a product container received by the housing and containing a product, a piston received in the housing in such a way that it can be displaced in a forward direction to dispense the product, a piston rod which acts on the piston in the forward direction, and a spring which acts on the piston rod in the forward direction, wherein, in one embodiment, the spring includes at least two adjacent spring sections each having a different buckling resistance in relation to the same length when the piston rod is a forward position and, in another embodiment, the appliance includes a spring guiding structure that is entrained or in use during a forward movement of the piston rod and secures the spring against buckling, wherein, when the piston rod is in the forward position, the guiding structure extends past an end of the rod.

9 Claims, 3 Drawing Sheets

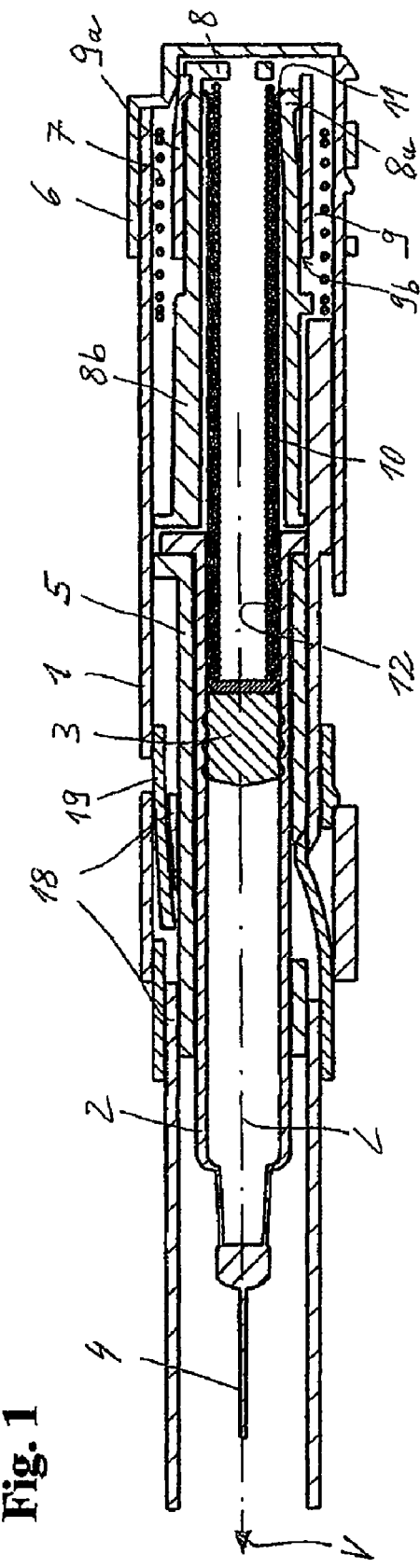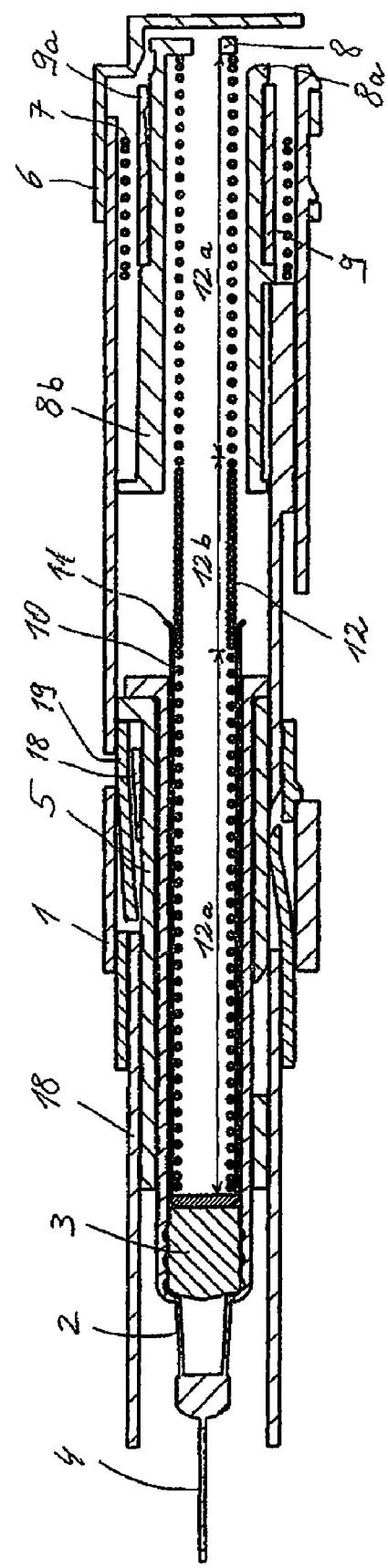

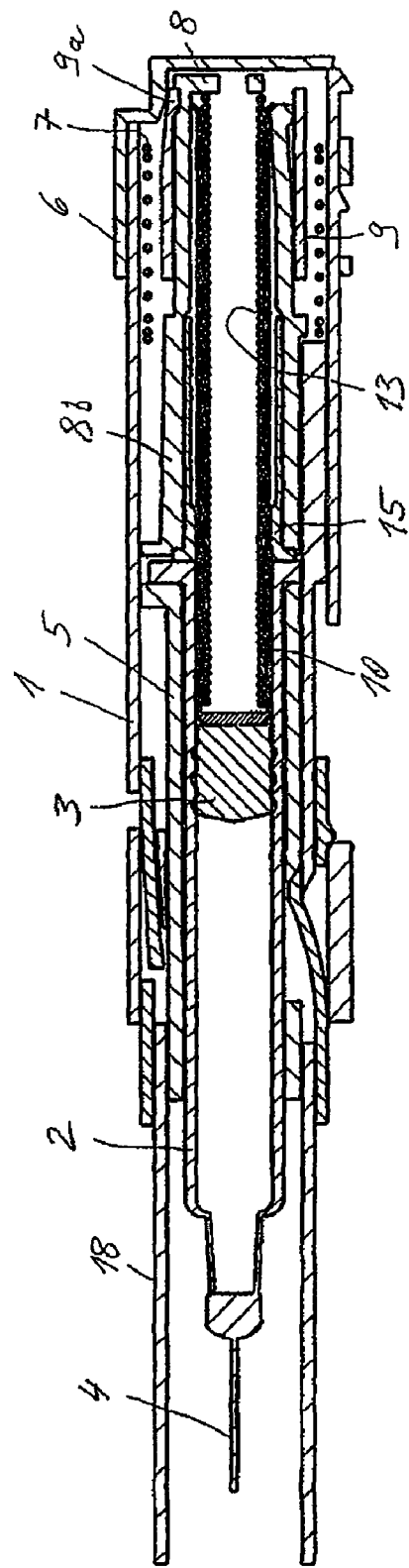
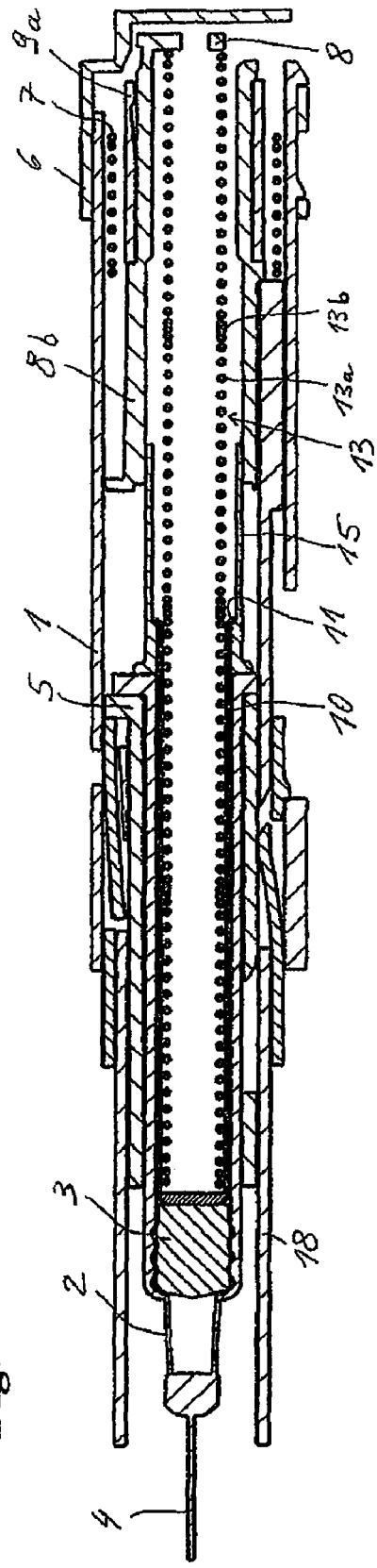
Fig. 3
Fig. 4

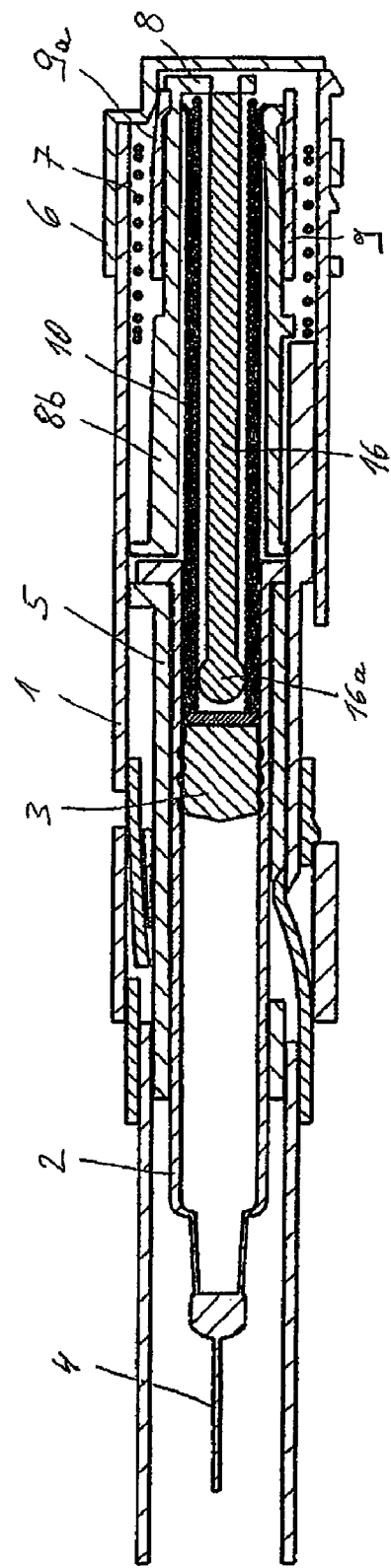
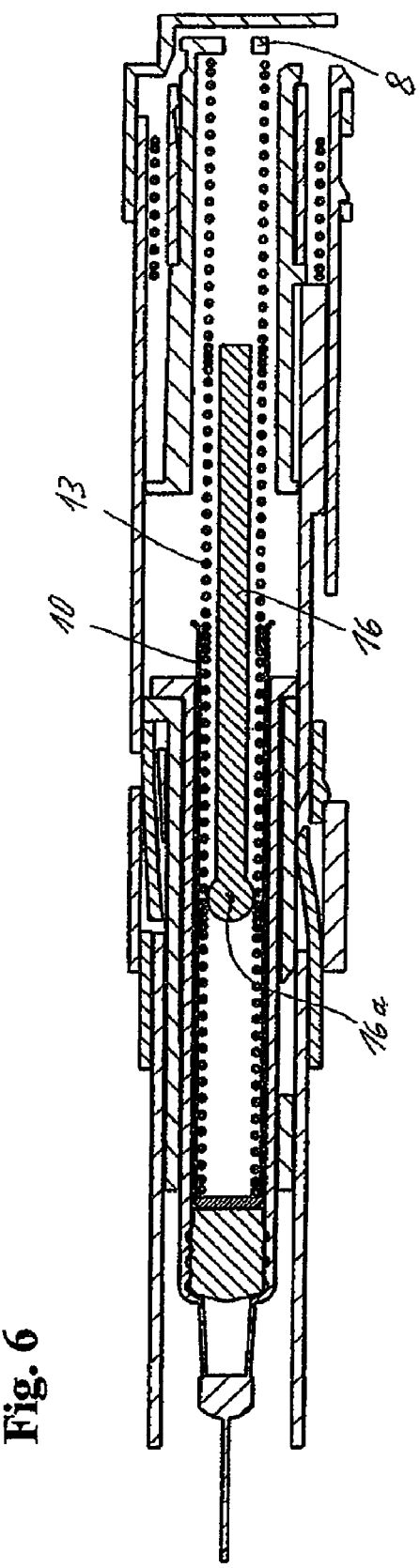

INJECTION DEVICE GUIDE SPRING

CROSS-REFERENCE TO RELATED APPLICATIONS

This application is a continuation of International Application No. PCT/CH2006/000017, filed on Jan. 11, 2006, which claims priority to German Application No. DE 20 2005 006 333.9 filed on Feb. 18, 2005, Germany Application No. DE 20 2005 003 847.4 filed on Mar. 10, 2005 and German Application No. DE 10 2005 017 477.9 filed on Apr. 15, 2005, the contents of all of which are incorporated in their entirety herein by reference.

BACKGROUND

The present invention relates to devices for injecting, administering, delivering, dispensing or infusing substances, and to methods for making and using such devices. More particularly, the present invention relates to an injection device with a spring, which serves as a driving spring for a conveying mechanism of the injection device. The present invention further relates to a spring used as a compression spring, e.g., a driving spring, for an injection device. The injection device may be an injection pen for administering insulin, growth hormones or an osteoporosis preparation in particular.

Mechanical springs, e.g., coil springs used as compression springs, are often used in injection pens as a means of driving a plunger in a container filled with the product to be injected in a forward drive direction, generally the distal direction. Such use as a driving spring is known from applications based on automatic injection devices in particular, which represents one type of injection device for the purpose of the present invention. Driving springs of well known automatic injectors are used not only to drive the plunger forward, but also to drive the injection needle during the injection. This being the case, the spring is therefore not only relaxed or the tension therein released by the distance over which the plunger has to be driven, but also by the length over which the needle has to be driven during the injection. In such cases, the driving spring of an automatic injector is longer than a driving spring which is used to drive the plunger only wherein the respective product containers must naturally be of the same length. The longer and slimmer the injection spring is, the more critical bending or buckling stresses can be, particularly in the case of automatic injectors, because the spring is typically required to expend a higher spring force in the forward drive direction than springs which only have to drive the plunger due to the fact that it has to drive the needle.

An automatic injector of the type to which the present invention relates in particular, although not exclusively, is known from German patent application No. 103 51 594. With this automatic injector, the plunger rod is provided in the form of a sleeve with a base or shoulder at its distal end and the driving spring projects into the sleeve in the distal direction onto the base or shoulder. Depending on the type of product container, the plunger rod sleeve is correspondingly slim and the spring is therefore slimmer. To prevent buckling or even just an outward deflection of the spring, the plunger rod co-operates with a support structure on which the spring is supported in the proximal direction to form a telescopic guide for the spring. The plunger rod and a guide portion of the support structure extend by an appropriate length in the distal direction in order to continue providing a reliable guide for the plunger rod even when the plunger rod has assumed its most distal position, having emptied the container.

SUMMARY

One object of the present invention is to improve the functional reliability of a driving spring of an injection device. Another object of the present invention is to provide a spring for use in an injection device which is less susceptible to defects.

In one embodiment, the present invention comprises an injection device comprising a housing, a product container received by the housing and containing a product to be injected, a piston received in the housing in such a way that it can be displaced in a forward direction to dispense the product, a piston rod which acts on the piston in the forward direction, and a spring which acts on the piston rod in the forward direction, wherein the spring includes at least two adjacent spring sections each having a different buckling resistance in relation to the same length when the piston rod is in a forward position.

In one embodiment, the present invention comprises a device for injecting a liquid product, comprising a housing, a product container mounted in the housing with a plunger accommodated in it, a plunger rod and a spring acting on the plunger rod. In some embodiments, the spring acts on the plunger rod in the distal direction, which in turn acts on the plunger. In some embodiments, the spring acts as a compression spring and extends lengthways in the distal direction, i.e., its axial or longitudinal length measured in the distal direction is significantly larger than its width measured perpendicular thereto.

In some embodiments, the present invention comprises a coil spring with coils extending adjacent to one another in a spiral about a spring axis, the coil spring being used as a compression spring for an injection device and comprising at least two axial spring portions, a first axial spring portion with a first buckling resistance in a relaxed state and a second axial spring portion with a second, higher buckling resistance in the relaxed state. In some embodiments, the coils in the second spring portion are more closely adjacent to each other than in the first spring portion when the spring is in the relaxed state. In some embodiments, the spring portions each have an axial length and second spring portion has a higher bending strength across the axial length than the first spring portion. In some embodiments, the spring has at least three axial spring portions adjacent to one another and the middle spring portion is more resistant to buckling than the other two spring portions. In some embodiments, the pitch of the coils is constant within each of the spring portions.

In some embodiments, the present invention comprises an injection appliance including a housing, a product container received by the housing and containing a product, a piston received in the housing in such a way that it can be displaced in a forward direction to dispense the product, a piston rod which acts on the piston in the forward direction, and a spring which acts on the piston rod in the forward direction, wherein, in one embodiment, the spring includes at least two adjacent spring sections each having a different buckling resistance in relation to the same length when the piston rod is a forward position and, in another embodiment, the appliance includes a spring guiding structure that is entrained or in use during a forward movement of the piston rod and secures the spring against buckling, wherein, when the piston rod is in the forward position, the guiding structure extends past an end of the rod.

In accordance with some embodiments of the present invention, the spring has at least two spring portions of differing buckling resistance disposed adjacent to one another in the distal direction, namely a first spring portion and a second spring portion with a different, e.g., higher, buckling resistance than the first spring portion. In some embodiments, the buckling resistance of the second spring portion is sufficiently high that a guide for the spring can be dispensed with in the second spring portion and may not be implemented in some preferred embodiments. In such embodiments, the plunger rod or the container guides or guide a distal spring portion, which may form the first spring portion or one of several first spring portions. While in some embodiments the second spring portion can be used to bridge a distance of the spring which requires no guide during and after driving the plunger rod forward, it is at least the first spring portion which drives the plunger rod forward because the spring is softer in the first spring portion than in the second spring portion due to the lower buckling resistance. Accordingly, in some embodiments, the difference in length between the tensed and the relaxed state of the spring is larger in the first spring portion than in the second spring portion.

In some preferred embodiments, the spring has at least one other axial spring portion with a lower buckling resistance. The at least one other spring portion may correspond to the first spring portion in terms of buckling resistance and spring stiffness. If the spring has at least two spring portions with a lower buckling resistance, for example two identical first spring portions in terms of spring stiffness and buckling resistance, which may be of the same or different lengths, the forward driving movement is advantageously distributed to these several axial spring portions with a lower buckling resistance. The second axial spring portion may bridge a distance without any guide whatsoever, although in some preferred embodiments, it is guided at one of its axial ends at least at both axial ends, including when the plunger rod is in the most distal position.

In some preferred embodiments, if the spring has two axial spring portions with a lower buckling resistance, the second axial spring portion is disposed between these two spring portions. In other embodiments, the spring has spring portions of higher buckling resistance axially alternating with spring portions of lower buckling resistance. Such a spring is able to bridge several distances which have no guide and optimum use can be made of the spring action within distances which are guided.

One spring, in accordance with the present invention, is a compression spring and is provided in the form of a coil spring with a plurality of coils, which extend in a spiral along a spring axis. The differing degrees of buckling resistance in such springs may be obtained in various ways. For example, the cross-section of the spring wire may be larger in the second axial spring portion than in the first axial spring portion, and the same applies if even more different axial spring portions are provided. However, in some preferred embodiments, the variation in buckling resistance is obtained by varying the pitch of the spring coils, in which case the pitch in the first spring portion is higher than in the second spring portion, at least when the spring is in the relaxed state, so that the coils in the second spring portion lie closer to one another than in the first spring portion. In some preferred embodiments, the spring is dimensioned so that the coils in the second spring portion lie against one another in a block when the plunger rod assumes its most distal position having emptied the product container. If the spring has several axial spring portions of lower buckling resistance or several spring portions of both types, what was said about the first and second spring portions above applies to the other axial spring portions.

In some embodiments, the buckling resistance of the spring portions is defined for the same axial length in each case for each spring portion, i.e., the buckling resistance is based on a unit of length. In the situation where spring portions have different lengths, the length of the shorter spring portion, or if there are more than two different spring portions, the length of the shortest spring portion, may be used as the reference length. If the different spring portions are homogeneous across their entire length, as in some preferred embodiments, the characteristic "buckling resistance" may simply be replaced by the characteristic "bending strength" which does not depend on length. However, in situations where the spring portions of differing buckling resistance are not homogeneous across their respective length, the higher buckling resistance of the at least one second spring portion is also combined with a higher bending strength across its length in each cross-section.

In some preferred embodiments, a spring in accordance with the present invention is used as the driving spring as described above. In principle, however, it may advantageously be installed in any situation where it is necessary to contend with bending or buckling stress.

Although a spring in accordance with the present invention may advantageously be used without any guide in the second spring portion or the several axial spring portions of higher buckling resistance, a guide or guide structure for the spring can be provided in accordance with the present invention. In some embodiments, the guide structure is driven with the plunger rod as it is driven forward. When the plunger rod assumes its most distal position having emptied the container, the spring projects in the proximal direction beyond the plunger rod and is prevented from buckling by the guide structure. The guide structure is advantageously may be used in combination with a spring in accordance with the present invention. If a guide structure is provided, however, it is also possible to use a conventional spring as an alternative, comprising axial spring portions each with an identical buckling resistance, e.g., an identical buckling resistance everywhere across the entire spring length.

A guide structure in accordance with the present invention may be of a bellows-type design, for example, guiding the spring at certain points. In some embodiment, the guide may be of an axially stiff design or generally tubular. In some preferred embodiments, the guide structure comprises a single part and, in combination with the plunger rod, forms a guide telescope with the plunger rod serving as a first telescopic portion and the guide structure serving as a second telescopic portion. In principle, the guide structure may also have several parts, and may itself form a guide telescope.

The plunger rod can advantageously be moved in the distal direction relative to the guide structure. So that providing the guide structure does not require making the injection device longer in the distal-proximal direction or at least making it necessary to make it considerably longer, it is of advantage if the plunger rod partially or totally overlaps with the guide structure in its most proximal position and the overlap is reduced by the forward driving action of the plunger rod.

In some preferred embodiments, the present invention may applied advantageously to automatic injectors, i.e., injection devices wherein an injection needle is automatically pushed forward relative to the housing when triggered, until it projects forward by a sufficient length beyond the housing or a needle guard which can be moved relative to the housing to permit an injection, and wherein the product is automatically conveyed out of the container when triggered. In particular, a spring in accordance with the present invention may constitute the driving spring of an automatic injector and drive the injection needle, beyond the container, and the plunger forward. The driving spring of an automatic injector of this type specifically extends along the distal or longitudinal direction, which means that automatic injectors may be susceptible to the problem of buckling or flexing of the spring to a specific degree unless counter-measures are taken.

BRIEF DESCRIPTION OF THE DRAWINGS

FIG. 1 shows a first exemplary embodiment of an injection device prior to triggering;

FIG. 2 shows the injection device of the first embodiment after triggering;

FIG. 3 shows a second exemplary embodiment of an injection device prior to triggering;

FIG. 4 shows the injection device of the second embodiment after triggering;

FIG. 5 shows a third exemplary embodiment of an injection device prior to triggering; and FIG. 6 shows the injection device of the third embodiment after triggering.

DETAILED DESCRIPTION

FIGS. 1 and 2 illustrate an injection device in accordance with one embodiment of the present invention. Both show the same longitudinal section, FIG. 1 showing an initial state prior to triggering and FIG. 2 after triggering. The injection device is an automatic injector, which automatically effects the entire injection once placed on the injection site and triggered, i.e., piercing by the injection needle and dispensing of a product or substance to be injected or delivered.

Disposed in a housing 1 of the injection device is a container 2 filled with the product to be injected, accommodated so that it is able to move in the distal direction V along a central longitudinal axis L of the injection device. The container 2 may be an ampoule of the type commonly used with such devices, with an outlet at a distal end and a plunger 3 which seals the container 2 at the proximal end. The plunger 3 is accommodated so that it can move in the container 2 along the axis L to dispense the product through an injection needle 4 fitted on the distal end of the container 2 and projecting in the distal direction V due to a driving action in the distal direction V. The injection needle 4 is provided in the form of a cannula, i.e., with a hollow cross-section, but could also have a solid cross-section with at least one flow passage at the outer or peripheral surface. The injection needle 4 is surrounded by a needle guard 18 extending beyond its distal tip. The needle guard 18 forms both a visible screen, i.e., it blocks any view of the injection needle 4, and serves as a protection against piercing by the injection needle 4.

The container 2 is accommodated in a container holder 5. The container holder 5 sits tightly surrounding the container 2. The housing 1 guides the container 5 so that it can move axially. The container 2 engages round the container holder 5 by a container flange formed at or near the proximal or rearward end so that a force acting on the container 2 in the distal direction V is transmitted to the container holder 5.

In addition to the plunger 3, a conveying mechanism of the injection device comprises a plunger rod 10 and a driving spring 12. The driving spring 12 is a coil spring and, when the injection device is triggered, acts as a compression spring in the distal or forward direction V on the plunger rod 10, which transmits the spring force to the plunger 3. The driving spring 12 projects in the distal direction V into the hollow cylindrical plunger rod 10, where it sits against a base of the plunger rod 10. The plunger rod 10 is provided in the form of a slim, thin-walled sleeve with a base which is likewise thin. The base could also be replaced by a narrow, inwardly projecting shoulder; it is merely necessary to ensure that the driving spring 12 is reliably supported. The base sits in a loose abutment contact with the rear face of the plunger 3. In the proximal direction, the driving spring 12 is supported on a support and guide structure 8. When the driving spring 12 is in the tensed state, virtually its entire length is accommodated in the plunger rod 10 and it projects or extends beyond the plunger rod 10 in the proximal direction as far as necessary for it to be supported.

The driving spring 12 is held in the tensed state by a retaining mechanism. The retaining mechanism can be released. It comprises a blocking element 6, a spring 7, the support and guide structure 8, a snapper 9a and a retaining element 11 connected to the plunger rod 10. The retaining element 11 is an outwardly directed flange formed on the end of the sleeve wall of the plunger rod 10. The retaining element 11 engages behind an elastic resilient lug 8a of the support and guide structure 8 when the device is in the initial state. In the initial state, the resilient lug 8a is bent elastically radially inwardly, engaging with the retaining element 11. Back-snapping is prevented by a co-operating surface of a snapper sleeve 9, which is an elastic flexible lug constituting the snapper 9. The snapper sleeve 9 is joined to the housing 1 so that it can not move axially and surrounds the support and guide structure 8. At its proximal end, its snapper 9a has a thicker region disposed radially inwardly, by which it locates in a recess in an external face of the support and guide structure 8. The sleeve-shaped blocking element 6 blocks the snapper 9a in this engagement. The spring 7 acts on the blocking element 6 in the proximal direction. In the initial state, the blocking element 6 is locked in the position blocking the snapper 9a. The lock can be released by operating a trigger element.

To trigger the injection device, the trigger element is operated and the lock of the blocking element 6 is released as a result. The blocking element 6 moves in the proximal direction relative to the housing 1, support and guide structure 8 and snapper 9a due to the force of the spring 7 and releases the snapper 9a. Since the force of the tensed driving spring 12 acts on the support and guide structure 8, the support and guide structures 8 pushes in the proximal direction against the snapper 9a, which is still engaged but has already been released by the blocking element 6, so that it bends elastically outwardly, thereby releasing the engagement between the snapper 9a and the support and guide structure 8. The recess of the support and guide structure 8 and the portion of the snapper 9a engaging in the recess are shaped so that the engaging portion is able to slide out of engagement due to the spring force of the support and guide structure 8 acting in the proximal direction by bending the snapper 9a outwardly.

After the engagement is released, the driving spring 12 pushes in the proximal direction in the initial phase after releasing the support and guide structure 8 until it reaches a stop 9b formed by the snapper sleeve 9. When the support and guide structure 8 has reached the stop position or, optionally, shortly before moving into the stop position, the resilient lug 8a, which until now has been in engagement with the retaining element 11, snaps radially outwardly out of engagement so that the plunger rod 10 is released. The driving spring 12 is now able to push the plunger rod 10 in the distal direction V relative to the housing 1. Due to the static friction acting between the plunger 3 and the side wall of the container 2, the container 2 and together with it the container holder 5 are moved in the distal direction V in what is now the second displacement phase after triggering. During this movement, the injection needle 4 moves out from the housing 1 into a farthest distal position. The forward movement is restricted by the container holder 5 moving into abutment with a cooperating stop. When the container holder 5 moves into abutment with the co-operating stop, the static friction between the plunger 3 and the container 2 is overcome, and the driving spring 12 pushes the plunger 3 in the container 2 forward in the distal direction V during a third displacement phase so that the product is dispensed. The displacement phases or movements described above may take place one after the other without any overlap or may at least partially overlap with one another in time. In some embodiments, the moved parts are mounted so that the conveying stroke of the plunger 3 does not start until the piercing movement of the injection needle 4 has ended.

FIG. 2 illustrates the injection device after an injection. The container 2 has been emptied. The plunger 3 and the injection needle 4 each assume their most distal position. The driving spring 12 is relaxed other than a minimum tension needed to drive the plunger 3 forwardly. In this state, the residual tension extends across a part of or the major part of the total length of the injection device measured from the distal end of the housing 1 as far as the proximal end of the injection device.

After the injection, and after the injection needle 4 has been removed from the body tissues and the injection device moved away form the injection site, the needle guard 18 snaps relative to the container holder 5 and the injection needle 4 in the distal direction as far as a guard position in which the needle guard 18 fully surrounds the injection needle 4 to beyond the tip. In the guard position, the needle guard 18 is locked in position prior to triggering the injection device, so that it is not able to move in the proximal direction relative to the injection needle 4. In the guard position after the injection, the lock is effected by an abutment contact of the proximal end of the needle guard 18 and a distal end of a locking element 19 as the needle guard 18 is moved with its proximal end in front of the locking element 19 after the injection needle 4 has been extracted, thereby releasing the pressure induced by the action of a spring, not illustrated. Prior to the injection, this movement of the needle guard 18 is prevented by a blocking mechanism which automatically releases as the container 2 is moved.

As may be seen from FIG. 2, the driving spring 12 has axial spring portions 12a and 12b, in which the spring coils lie next to one another at different distances. In the middle spring portion 12b, all the spring coils lie in a block in contact with one another in the axial direction in the state of residual tensioning, while the spring coils in the two outer spring portions 12a are spaced apart from one another. The two outer spring portions 12a differ from one another in terms of their length. Due to the fact that the spring coils in the middle spring portion 12b lie closer together, a higher buckling resistance is obtained across the length of the spring portion 12b than in the two outer spring portions 12a, and their buckling resistance is defined on the basis of the length of the middle spring portion 12b compared with each of the part-portions. The higher buckling resistance also means higher spring stiffness, so that the spring work needed to drive the plunger 3 and the injection needle 4 is effected in the two outer axial spring portions 12a. There, the driving spring 12 expands axially when relaxed. In the embodiment illustrated as an example in which the spring coils in the middle spring portion 12b still lie in a block when the plunger 3 is in its most distal position, the entire spring work is effected in the two outer spring portions 12a. In other embodiments, however, it would also be conceivable for the driving spring 12 to be relaxed in the middle spring portion 12b, albeit less than in the outer spring portions 12a and at the cost of buckling resistance.

In the spring portions 12a, the driving spring 12 is guided or at least secured during the entire driving movement. The plunger rod 10 serves as a guide because the spring coils lie against its internal surface. The support and guide structure 8 forms a guide in the wider sense, i.e., it prevents excessive bending or buckling of the proximal spring portion 12a. To this end, the support and guide structure 8 forms a guide portion 8b, on the internal surface of which the plunger rod 10 is guided via its retaining element 11. Accordingly, there is a slight radial distance between the driving spring 12 and the guide portion 8b once the plunger rod 10 has been extracted but it is sufficient to prevent the driving spring 12 from bending.

When the plunger rod 10 assumes a selected or its most distal position as illustrated in FIG. 2, it is extracted from the guide portion 8b and there is an axial clearance distance between the plunger rod 10 and the support and guide structure 8. The driving spring 12 is neither guided nor secured to prevent bending or buckling across the length of this distance. The spring portion 12b bridges this distance, thereby also preventing any excessive bending or buckling of the driving spring 12 across its length. To improve reliability, the spring portion 12b projects in the distal direction V by a short distance farther into the plunger rod 10 and in the proximal direction also a short distance into the guide 8b. This further enhances reliability of the prevention of bending and buckling.

In respect of the driving spring 12 in the embodiment described as an example herein, it should be pointed out that it may be wound from the same spring wire with the same overall cross-section and with the same material properties across its entire length. The increased buckling resistance is therefore exclusively attributable to the smaller pitch of the coils in the spring portion 12b. The pitch in the spring portions 12a overall is the same. The pitch is also constant in the spring portion 12b. In the middle portion, therefore, the bending resistance is higher overall than in the outer spring portions 12a.

The axial distance between the plunger rod 10 and the support and guide structure 8 corresponds to the length by which the injection device is shorter than an otherwise identical injection device in which the driving spring is guided or secured across its entire length in the conventional manner in the relaxed state.

If the container holder 5 or optionally the container 2 directly is not locked in its most distal position to prevent a movement in the proximal direction relative to the housing 1, the specific buckling resistance of the spring 13 prevents the spring 13 from buckling, if a force directed in the proximal direction is applied to the needle guard 18 and acts on the container 2 and ultimately the spring 13 due to the abutment contact between the needle guard 18 and locking element 19 and its abutment contact with the container holder 5. However, the buckling resistance of the spring 13 is also advantageous even during the piercing movement of the injection needle 4 and the conveying movement of the plunger 3.

FIGS. 3 and 4 illustrate a second exemplary embodiment of an injection device, in which, when the plunger 10 is extracted, the axial distance is bridged by a guide structure 15 which prevents any excess bending or buckling of the driving spring 13 in this region. FIG. 3 illustrates the injection device in the initial state prior to triggering and FIG. 4 shows the device after triggering and emptying the container 2.

The driving spring 13 has adjacent spring portions 13a and 13b alternating in the axial direction wherein the buckling resistance of the spring portions 13b is higher than that of the spring portions 13a based on identical lengths in each case.

The spring portions 13a and 13b are respectively shorter than the corresponding spring portions 12a and 12b of the first embodiment described above. The more buckling resistant spring portions 13b are significantly shorter than the axial distance between the support structure 8 and the plunger rod 10 disposed in the most distal position, and the guide structure 15 is therefore provided to reliably prevent any excessive bending or buckling of the driving spring 13 in this region.

Apart from the driving spring 13 and the guide structure 15 as well as an associated modification made to the guide portion 8b, the injection device of the second embodiment corresponds to the embodiment described as a first example and the same reference numbers are used to denote the same components. Reference may therefore be made to the descriptions given above.

The guide structure 15 is an integral, intrinsically stiff sleeve, which is mounted in a sliding seating on the external surface of the plunger rod 10. It has two sleeve portions merging into one another, namely a distal portion with a first internal diameter and a proximal sleeve portion with a second, larger internal diameter. The proximal portion is longer than the distal portion. By its distal sleeve portion, the guide structure sits in sliding contact on the plunger rod 10. It is also in contact with it by its distal end in the initial state as well as the rear face of the container 2 at least when the plunger rod 10 is disposed in the distal direction V. The external face of the guide structure 15 is smooth and is in sliding contact with an internal face of the guide portion 8b. In principle, however, an annular gap could also be formed between the guide structure 15 and the guide portion 8b.

In the initial state, the plunger rod 10 fully overlaps with the guide structure 15. The guide structure 15 is also at least substantially accommodated in the support and guide structure 8. The guide structure 15 does not therefore requires that the injection device has to be made longer.

When the injection device is triggered, the displacement or movement sequence described in connection with the first exemplary embodiment is set in motion. The sliding seating of the guide structure 15 on the plunger rod 10 is designed so that the guide structure 15 is driven by the plunger rod 10 as well during the driving movement of the container 2 and always remains in contact with the container 2. Once the container holder 5 has reached its stop position, the plunger rod 10 pushes the plunger 3 in the distal direction V during the final displacement phase until the container 2 has been emptied. During the final displacement phase, the plunger rod 10 moves in sliding contact relative to the guide structure 15 until it has reached its most distal position. The guide structure 15 forms a driving shoulder due to the transition between the distal portion and the proximal portion, against which the retaining element 11 of the plunger rod 10 moves into abutment at least when the plunger rod 10 is in the most distal position. This driving engagement ensures that the guide structure 15 is moved during the injection far enough in the distal direction V to bridge the resultant distance between the plunger rod 10 and the support and guide structure 8.

A third exemplary embodiment of an injection device is illustrated in FIGS. 5 and 6. The injection device based on the third embodiment has a guide structure 16, which is accommodated inside the plunger rod 10 when the device is in the initial state. Apart from the guide structure 16, the injection device of the third exemplary embodiment is the same as the injection device of the second embodiment and reference may be made to the descriptions given above.

The guide or guide structure 16 is provided in the form of a guide bar. It is approximately the same length as the tensed driving spring 13. An engagement element 16a is formed on the distal end of the guide structure 16. The engagement element 16a is a thicker region and in this embodiment is a spherically shaped thicker region of the guide bar. The engagement element 16a sits in a pressing contact with the driving spring 13. The thickness of the engagement element 16a as measured perpendicular to the longitudinal axis L is dimensioned so that the coils of the driving spring 13 are able to slide over the engagement element 16a in the distal direction V during a driving movement of the plunger rod 10, but the sliding movement is made more difficult to the degree that the guide structure 16 is driven along a part of the distance traveled by the plunger rod 10 before reaching its most distal position. The engagement element 16a lightly engages in the intermediate space between axially adjacent spring coils. When the plunger rod 10 is in its most distal position, the guide structure 16 bridges the axial clearance distance between the plunger rod 10 and the support and guide structure 8, which also reliably prevents any bending or buckling, namely due to a guiding action, i.e., a securing action within the driving spring 13.

Embodiments of the present invention, including preferred embodiments, have been presented for the purpose of illustration and description. They are not intended to be exhaustive or to limit the invention to the precise forms and steps disclosed. The embodiments were chosen and described to provide the best illustration of the principles of the invention and the practical application thereof, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

The invention claimed is:

1. An injection device comprising:
   a) a housing;
   b) a product container accommodated by the housing, in which a plunger is accommodated so that it can be moved in a distal direction to dispense product;
   c) a plunger rod acting on the plunger in the distal direction; and
   d) a spring acting on the plunger rod in the distal direction, wherein the spring comprises at least two adjacent spring portions which have a different buckling resistance for an identical length when the plunger rod is in a distal position, and wherein the spring is a coil spring with coils extending adjacent to one another in a spiral about a spring axis, which coil spring is used as a compression spring for an injection device and wherein the at least two spring portions comprise a first axial spring portion with a first buckling resistance in a relaxed state and a second axial spring portion with a second, higher buckling resistance in the relaxed state; and
   e) wherein the coils in the second spring portion lie next to one another and in contact with one another in a block when the plunger rod is in the distal position such that the second, higher buckling resistance is obtained across the second spring portion.

2. The injection device as claimed in claim 1, wherein, of the at least two spring portions, the spring portion with the higher buckling resistance overlaps a proximal end portion of the plunger rod or extends in the distal direction as far as the proximal end of the plunger rod when the plunger rod assumes the distal position.

3. The injection device as claimed in claim 1, further comprising a guide portion which overlaps the plunger rod when the plunger rod is in a proximal position, and the plunger rod moves away from the position overlapping with the guide portion when driven in the distal direction and a proximal end of the plunger rod is spaced at a distance axially apart from the guide portion when the plunger rod is in the distal position.

4. The injection device as claimed in claim 1, wherein the housing comprises a mount for the product container so that the container can move in the distal direction and the spring acts on the product container in the distal direction.

5. The injection device as claimed in claim 1, wherein the coils in the second axial spring portion are more closely adjacent to each other than in the first axial spring portion when the spring is in the relaxed state.

6. The injection device as claimed in claim 1, wherein the spring portions each have an axial length and the second axial spring portion has a higher bending strength across the axial length than the first axial spring portion.

7. The injection device as claimed in claim 1, wherein the spring has at least three axial spring portions adjacent to one another and the middle axial spring portion is more resistant to buckling than the other two axial spring portions.

8. The injection device as claimed in claim 1, wherein the pitch of the coils is constant within each of the spring portions.

9. The injection device as claimed in claim 1, wherein the pitch of the coils is constant within each of the spring portions.

* * * * *